US012616833B2

(12) United States Patent
Tass

(10) Patent No.: US 12,616,833 B2
(45) Date of Patent: May 5, 2026

(54) MEDICAL TREATMENT DEVICE AND METHOD FOR STIMULATING NEURONS OF A PATENT TO SUPPRESS A PATHOLOGICALLY SYNCHRONOUS ACTIVITY THEREOF

(71) Applicant: GRETAP AG, Zug (CH)

(72) Inventor: Peter Alexander Tass, Tegernsee (DE)

(73) Assignee: GRETAP AG, Zug (CH)

( * ) Notice: Subject to any disclaimer, the term of this patent is extended or adjusted under 35 U.S.C. 154(b) by 717 days.

(21) Appl. No.: 17/905,428

(22) PCT Filed: Mar. 3, 2021

(86) PCT No.: PCT/EP2021/055278

§ 371 (c)(1),
(2) Date: Sep. 1, 2022

(87) PCT Pub. No.: WO2021/175898

PCT Pub. Date: Sep. 10, 2021

(65) Prior Publication Data

US 2023/0264018 A1 Aug. 24, 2023

Related U.S. Application Data

(60) Provisional application No. 62/984,454, filed on Mar. 3, 2020.

(51) Int. Cl.
*A61N 1/36* (2006.01)
*A61H 23/02* (2006.01)

(52) U.S. Cl.
CPC ..... *A61N 1/36025* (2013.01); *A61H 23/0245* (2013.01); *A61H 2201/1607* (2013.01)

(58) Field of Classification Search
CPC ............ A61N 1/36025; A61H 23/0245; A61H 2201/1607; A61H 2201/0157;
(Continued)

(56) References Cited

U.S. PATENT DOCUMENTS 4,685,448 A * 8/1987 Shames ................ G09B 21/009
600/23
9,014,824 B2 4/2015 Kroll-Orywahl et al.
(Continued)

FOREIGN PATENT DOCUMENTS

CA 3011993 A1 8/2017
GB 2548148 A 9/2017
(Continued)

OTHER PUBLICATIONS

International Search Report in PCT International Application No. PCT/EP2021/055278 mailed Jun. 23, 2021.

*Primary Examiner* — James M Kish
*Assistant Examiner* — Natasha Patel
(74) *Attorney, Agent, or Firm* — Greenberg Traurig LLP; Roman Fayerberg; Richard Brooks

(57) ABSTRACT

The present invention pertains to a medical treatment device (10) for stimulating neurons of a patient to suppress a pathologically synchronous activity of the neurons. The device (10) comprises a non-invasive stimulation unit (12) configured for simultaneously administering at least one acoustic stimulus and at least one non-acoustic stimulus to a patient's body, each of which is configured to suppress the pathologically synchronous activity when being administered to the patient's body.

10 Claims, 4 Drawing Sheets

(58) Field of Classification Search
CPC ........ A61H 2201/1207; A61H 2205/02; A61H
23/008; A61M 2021/0022; A61M
2021/0027; A61M 2021/0044; A61M
2021/0066; A61M 2021/0072; A61M
2209/088; A61M 21/00
See application file for complete search history.

(56) References Cited

U.S. PATENT DOCUMENTS

| | | | |
|---|---|---|---|
| 2013/0090519 A1* | 4/2013 | Tass ........................ | A61H 23/00 |
| | | | 600/27 |
| 2015/0126802 A1* | 5/2015 | Lim ................... | A61N 1/36167 |
| | | | 607/45 |
| 2015/0297444 A1* | 10/2015 | Tass ........................ | A61B 5/245 |
| | | | 607/96 |
| 2017/0368342 A1* | 12/2017 | Tass ..................... | A61B 5/4082 |
| 2019/0200888 A1 | 7/2019 | Poltorak | |
| 2019/0387335 A1* | 12/2019 | Hughes ................. | A61M 21/02 |

FOREIGN PATENT DOCUMENTS

| | | | |
|---|---|---|---|
| JP | 2013523357 A | 5/2014 |
| WO | 2011/127918 A1 | 10/2011 |
| WO | 2013/158208 A2 | 10/2013 |
| WO | 2015187712 A1 | 12/2015 |
| WO | 2019243634 A1 | 12/2019 |

* cited by examiner

MEDICAL TREATMENT DEVICE AND METHOD FOR STIMULATING NEURONS OF A PATENT TO SUPPRESS A PATHOLOGICALLY SYNCHRONOUS ACTIVITY THEREOF

CROSS-REFERENCE TO RELATED APPLICATION

This application is a U.S. national phase filing under 35 U.S.C. 371 of International Application No. PCT/EP2021/055278, filed Mar. 3, 2021, which claims the benefit of and priority to U.S. Provisional Application No. 62/984,454 filed Mar. 3, 2020, the contents of each of which are hereby incorporated herein by reference in their entireties.

TECHNICAL FIELD

The invention relates to a medical treatment device and a respective method for stimulating neurons of a patient to suppress a pathologically synchronous activity of the neurons.

TECHNOLOGICAL BACKGROUND

Several brain disorders, such as Parkinson's disease, are characterized by abnormally strong synchronous activity of neurons, i.e. strongly synchronized neuronal firing or bursting. Besides Parkinson's disease, this may also apply, for example, to essential tremor, dystonia, dysfunction after stroke, epilepsy, depression, migraine, tension headache, obsessive-compulsive disorder, irritable bowel syndrome, chronic pain syndromes, pelvic pain, dissociation in borderline personality disorder and post-traumatic stress disorder.

The pharmacological treatment for Parkinson's disease with, for example, L-DOPA may have limited therapeutic effects and it may cause significant long-term side effects. High-frequency Deep Brain Stimulation (DBS) for Parkinson's disease is a standard for medically refractory patients in advanced stages of Parkinson's disease. However, DBS requires surgical procedures associated with a significant risk. For instance, depth electrode implantation in dedicated target areas in the brain may cause bleedings. Furthermore, standard continuous high-frequency DBS may cause side effects.

Further, non-invasive vibrotactile stimulation treatments are known to counteract Parkinsonian signs, which may be applied to a head region of a patient. By doing so, vibrotactile stimulations are administered to an outer surface of the patient's head so as to generate vibrotactile stimuli which aim on affecting a pathological activity of a patient's neuronal population, in particular in a patient's brain or spinal cord. Such techniques are known as coordinated reset stimulation which allow for counteracting abnormal synchrony of the neuronal population by desynchronization. Typically, for generating the vibrotactile stimuli, vibrotactile stimulation elements fastened to the patient's head are employed and actuated.

Typically, upon actuating the vibrotactile stimulation elements, in addition to vibrotactile stimuli, also acoustic stimuli are perceived by the patient. This is caused by sound waves generated upon actuation of the stimulation elements which are conducted to the patient's inner ear through air and bone conduction. However, these acoustic stimuli constitute undesired side effects which are usually experienced as annoying and unpleasant by the patient, thereby reducing compliance. This particularly applies when the treatment is employed frequently, e.g. for long hours every day during weeks or months.

SUMMARY OF THE INVENTION

Starting from the prior art, it is an objective to provide an improved non-invasive medical treatment device and a respective method enabling to effectively suppress pathologically synchronous activities of a patient's neuronal population.

This object is solved by means of a medical treatment device and a method according to the independent claims. Preferred embodiments are set forth in the present specification, Figures as well as the dependent claims.

Accordingly, a medical treatment device is provided for stimulating neurons of a patient to suppress a pathologically synchronous activity of the neurons. The medical treatment device comprises a non-invasive stimulation unit configured for simultaneously administering at least one acoustic stimulus and at least one non-acoustic stimulus to a patient's body, each of which is configured to suppress the pathologically synchronous activity when being administered to the patient's body.

Furthermore, a medical treatment method for stimulating neurons of a patient to suppress a pathologically synchronous activity of the neurons is provided. The method comprises the step of non-invasively and simultaneously administer at least one acoustic stimulus and at least one non-acoustic stimulus to a patient's body, each of which is configured to suppress the pathologically synchronous activity.

The proposed method refers to method features corresponding to those features defined in connection with the medical treatment device. Thus, technical features which are defined in the present disclosure in connection with the medical treatment device may also relate and be applied to the proposed method, and vice versa.

BRIEF DESCRIPTION OF THE DRAWINGS

The present disclosure will be more readily appreciated by reference to the following detailed description when being considered in connection with the accompanying drawings in which.

DETAILED DESCRIPTION OF PREFERRED EMBODIMENTS

Figure 1:
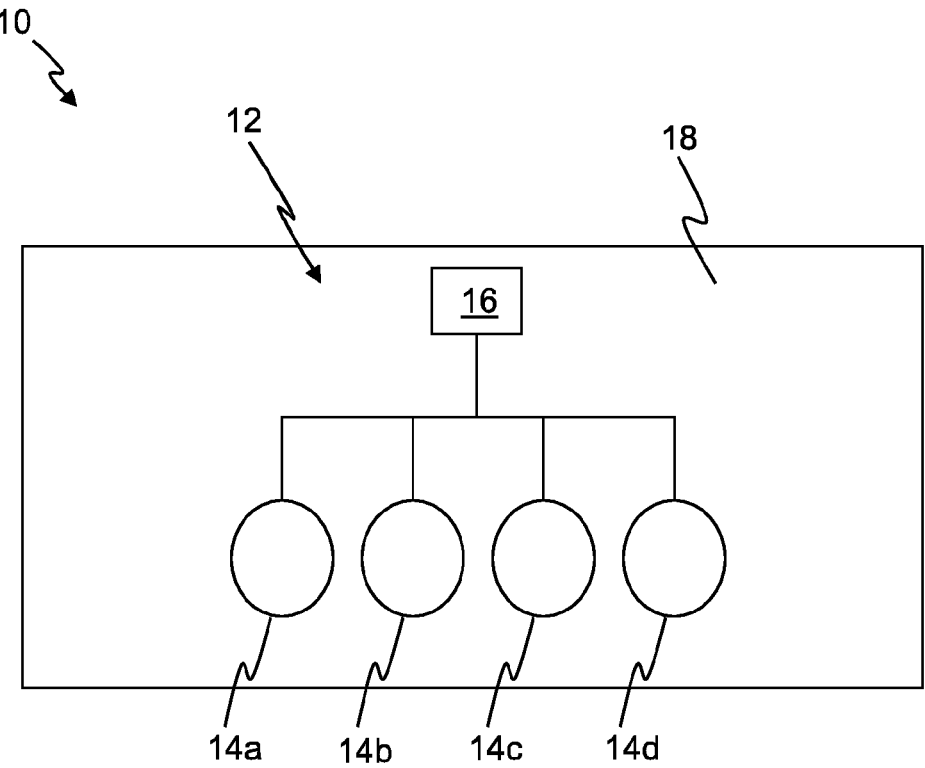
FIG. 1 is a schematic illustration of a medical treatment device for stimulating neurons of a patient to suppress a pathologically synchronous activity.

In the following, the invention will be explained in more detail with reference to the accompanying Figures. In the Figures, like elements are denoted by identical reference numerals and repeated description thereof may be omitted in order to avoid redundancies.

FIG. 1 schematically shows a medical treatment device 10 configured for stimulating neurons of a patient to suppress a pathologically synchronous activity of the neurons.

The device 10 is intended to be used for the treatment of migraines, headaches, depression, obsessive-compulsive disorders, borderline personality disorders, Parkinson's disease, but is not limited to these applications. Rather, the proposed medical treatment device 10 may further be used for the treatment of other neurological or psychiatric diseases, such as essential tremors, dystonia, epilepsy, tremors as a result of Multiple Sclerosis as well as other pathological tremors, movement disorders, diseases of the cerebellum, Tourette syndrome, functional disorders following a stroke, spastics, tinnitus, sleep disorders, schizophrenia, irritable colon syndrome, addictive disorders, personality disorders, attention deficit disorder, attention deficit hyperactivity syndrome, gaming addiction, neuroses, eating disorders, burnout syndrome, fibromyalgia, migraine, cluster head ache, neuralgia, ataxy, tic disorder or hypertension, etc.

The aforementioned diseases can be caused by a disorder of the bioelectric communication of groups of neuronal cells which are connected to one another in specific circuits. Hereby, a neuron population generates a continuous pathological neuronal activity and a pathological connectivity (network structure) possibly associated therewith. In this respect, a large number of neurons form synchronous action potentials. This means that the concerned neurons fire or burst excessively synchronously. In addition, the pathological neuron population has an oscillating neuronal activity, this means that the neurons fire or burst rhythmically. In the case of neurological or psychiatric diseases, the mean frequency of the pathological rhythmic activity of the concerned groups of neurons approximately may be in the range of 1 Hz to 30 Hz, but may, however, also be outside of this range. By contrast, the neurons of healthy people fire or burst qualitatively differently, for example, in an uncorrelated manner.

In other words, each of the aforementioned diseases may be characterized by at least one neuronal population in the brain or spinal cord of the patient which has a pathological synchronous neuronal activity. For suppressing such a pathologically synchronous activity, the medical treatment device is configured to stimulate the affected neuronal population so as to cause the affected neural population to fire or burst in an uncorrelated manner, i.e. non-synchronously. Such treatment techniques are also referred to as coordinated reset stimulation.

For acting onto the patient's body and thus for providing stimulation of the patient's neurons, the device 10 comprises a non-invasive stimulation unit 12 which is configured to provide different stimuli to the patient's body. In the context of the present disclosure, the term "non-invasive" means that the medical treatment device 10, i.e. the stimulation unit 12, deploys a non-invasive procedure to achieve intended therapeutic effects. In other words, the suggested medical treatment device 10 does not require implantation of components into the patient's body, i.e. which would be associated with an intervention procedure.

The stimulation unit 12 is designed and configured for simultaneously administering at least one acoustic stimulus and at least one non-acoustic stimulus to a patient's body, each of which is configured to suppress the pathologically synchronous activity when being administered to the patient's body. More specifically, the stimulation unit 12 is designed for being capable of simultaneously generating a plurality of different acoustic and non-acoustic stimuli. For doing so, the stimulation unit 12 comprises a plurality of stimulating elements 14a-d, in particular at least two stimulating elements, which are configured to generate acoustic and non-acoustic stimuli to be administered to the patient's body. As can be gathered from FIG. 1, the shown medical treatment device 10 comprises at least four stimulating elements 14a-d, but is not limited to this number of stimulating elements 14. It is pointed out that satisfying therapeutic effects may also be achieved with a medical treatment device 10 having less or more than four stimulating elements 14. Thus, according to another configuration, the stimulation unit 12 may include, for example, at least two, in particular between 3 and 8 or more, such as 10 or 20, stimulating elements 14. In one configuration, the stimulating unit 12 may comprise 3 or 5 stimulating elements.

For properly operating the different stimulating elements 14a-d, the stimulation unit 12 further comprises a control unit 16 which is configured to selectively actuate the stimulating elements 14a-d. In this way, individual stimulating elements 14a-d can be actuated independently from one another. Further, the control unit 16 is configured to variably actuate the stimulating elements 14a-d so as to generate different stimuli, i.e. in terms of stimuli duration, vibration frequency, vibration amplitude, etc. The control unit 16 is connected to each one of the stimulating elements 14a-d via a connecting wire, through which control signals are guided for actuating the stimulating elements 14 a-d.

As can be gathered from FIG. 1, the stimulation unit 12 is embedded or comprised in a strap or band 18 which is configured to be releasably and adjustably fastened to a patient's body, e.g. by means of Velcro fastener. Specifically, the band 18 is designed such that, in a state in which the band 18 is fastened to the patient's body, the stimulating elements 14a-d are arranged at different sites of a patient's body, i.e. spaced apart from one another. For example, the medical treatment device 10 may be provided such that, in the fastened state of the medical treatment device 10, the plurality of stimulating elements 14a-d are arranged in at least one array so as to position the stimulating elements 14a-d to predefined regions onto the surface of the patient's body, respectively, so as to achieve the desired therapeutic effect.

Figure 2:
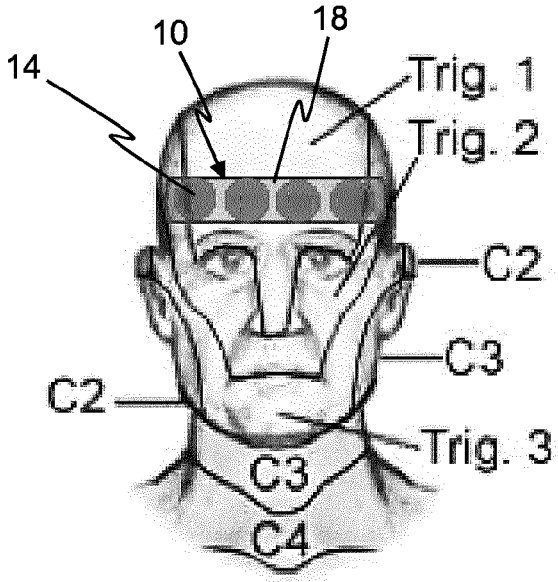
FIG. 2 schematically shows a use of the medical treatment device depicted in FIG. 1 for providing stimulation to a patient's forehead.

FIG. 2 depicts one embodiment of the medical treatment device 10 which is provided in the form of a headband configured for being fastened to the patient's forehead. In this configuration, the medical treatment device 10 is intended to be used for the treatment of migraines, headaches, depression, obsessive-compulsive disorders, borderline personality disorder and/or other psychiatric disorders. As can be gathered from FIG. 2, in this configuration, the medical treatment device 10 comprises four stimulating elements 14 arranged in a linear array which, in a state in which the medical treatment device 10 is fastened to the patient's forehead, are arranged in the region of the patient's trigeminal skin segment so as to stimulate the ophthalmic or trigeminal nerve, in particular the first branch of the trigeminal nerve denoted by "Trig. 1" in FIG. 2. In this way, in the fastened state of the medical treatment device 10, the stimulation unit 12 is configured to provide the acoustic stimuli to the patient's inner ear and the non-acoustic stimuli to a patient's skin in the region of the first branch of the trigeminal nerve Trig.1. In FIG. 2, also the second branch Trig. 2 and the third branch Trig. 3 of the trigeminal nerve as well as the C2 to C4 dermatomes are illustrated. In a further configuration, the shown medical treatment device 10 may comprise two arrays of stimulating elements 14, e.g. each of which comprises four stimulating elements 14 arranged in a line.

Figure 3:
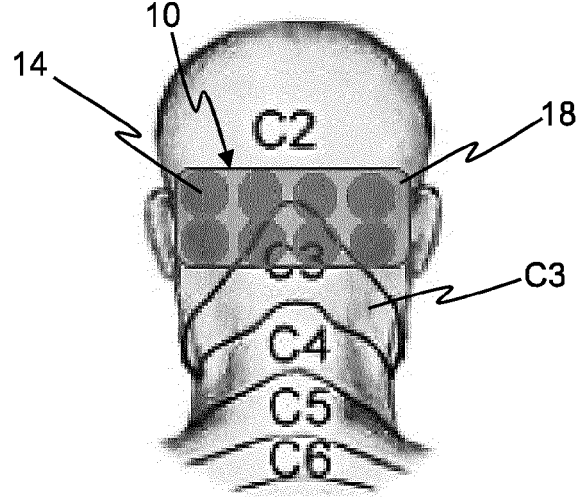
FIG. 3 schematically shows a further use of the medical treatment device depicted in FIG. 1 for providing stimulation of a patient's occiput.

FIG. 3 depicts another embodiment of the medical treatment device 10 which is provided in the form of a headband configured for being fastened to the patient's occiput. In this configuration, the medical treatment device 10 is intended to be used for the treatment of dysphagia (swallowing problems) and/or sialorrhea (excessive drooling), e.g. due to Parkinson's disease. As can be gathered from FIG. 3, in this configuration, the medical treatment device 10 comprises eight stimulating elements 14 arranged in two arrays, each of which comprises four stimulating elements 14 arranged in a line. In the fastened state of the medical treatment device 10 in which it is fastened to the patient's occiput, the stimulating elements 14 are arranged so as to stimulate the C2 and C3 dermatome as depicted in FIG. 3. In this way, in the fastened state of the medical treatment device 10, the stimulation unit 12 is configured to provide the acoustic stimuli to the patient's inner ear and the non-acoustic stimuli to a patient's skin in the region of the C2 and C3 dermatome. In FIG. 3, also the C4 to C6 dermatomes are illustrated.

In a further embodiment, the medical treatment device 10 may be provided in the form of a headband which combines the above embodiments depicted in FIGS. 2 and 3. Accordingly, in this configuration, the medical treatment device 10 is configured to stimulate the patient's forehead and occiput and may comprise at least two or four stimulating elements for stimulating the patient's forehead and at least two or four stimulating elements for stimulating the patient's occiput.

In the following, characteristics of the stimulation unit 12, in particular in view of its structural configuration and operation, interlinked to the present invention are further specified which apply to each one of the above described embodiments of the medical treatment device 10.

As set forth above, the stimulation unit 12 comprises the plurality of stimulating elements 14a-d which is configured to generate the acoustic and non-acoustic stimuli. In general, the terms "stimulus" or "stimuli" refer to excitations capable of being sensed by the patient's body, i.e. by respective receptors, e.g. in the eyes, the ears and/or the skin of the patient depending of the stimuli's modality, from whom they are guided to a patient's nerve system causing an actuation of neurons in the patient's brain or spinal cord. In the context of the present disclosure, it is differentiated between two modalities of stimuli, i.e. between acoustic and non-acoustic stimuli.

In general, the term "acoustic stimuli" refer to excitations to be sensed by receptors provided in the ear, in particular the inner ear, of the patient. Typically, these excitations are provided to the inner ear in the form of sound waves through air and bone conduction. To that end, in the context of the present disclosure, the term "non-acoustic stimuli" refer to any stimuli which do not constitute acoustic stimuli. For example, non-acoustic stimuli may refer to any one of mechanical stimuli, in particular tactile or vibratory stimuli, optical stimuli, electric stimuli and thermal stimuli. These stimuli may be sensed by corresponding receptors, for example, in the patient's skin or eyes.

As set forth above, the stimulation unit 12 is configured and designed for simultaneously administering at least one acoustic stimulus and at least one non-acoustic stimulus to a patient's body, wherein each one of the at least one acoustic stimulus and non-acoustic stimulus is configured to suppress the pathologically synchronous activity when being administered to the patient's body. In other words, each one of the acoustic and non-acoustic stimulus are configured to perform coordinated reset stimulation. In one operating mode of the medical treatment device 10, the non-acoustic stimuli may be configured to suppress the pathologically synchronous activity when being administered to the patient's body, while the acoustic stimuli may not be configured to suppress the pathologically synchronous activity when being administered to the patient's body.

More specifically, the stimulating unit 12 is provided such that the at least one acoustic stimulus is configured to suppress a pathologically synchronous activity of a first neuronal sub-population when being administered to the patient's body. Further, the stimulating unit 12 is provided such that at least one non-acoustic stimulus is configured to suppress a pathologically synchronous activity of a second neuronal sub-population which is different or delimited from the first neuronal population when being administered to the patient's body.

For being capable of suppressing the neuronal population affected by the pathologically synchronous activity, each one of the acoustic and non-acoustic stimuli is provided so as to at least partially cause actuation of the affected neuronal population upon being sensed by corresponding receptors in the patient's body and guided to its nerve system. For doing so, the modality and characteristic of the generated stimuli as well as the intended location at which they are to be induced into the patient's body are respectively set as described in the following in more detail.

In the shown configurations, for providing the non-acoustic stimuli, the stimulation unit 12 is configured to generate tactile or vibratory stimuli, also referred to vibrotactile stimuli, to be administrated to corresponding receptors in the patient's skin, in particular in the head region of the patient. In general, the human skin comprises different types of mechanoreceptive afferent units capable of sensing tactile or vibratory stimuli. Typically, the distribution and density of the different types of mechanoreceptors differs in dependence on the position on the human skin.

For selectively stimulating desired mechanoreceptive afferent units of the patient, the stimulation unit 12 comprises a plurality of vibrotactile stimulating elements 14a-d configured for generating the non-acoustic stimuli in the form of vibrotactile stimuli. Specifically, each one of the vibrotactile stimulating elements 14a-d is configured to oscillatingly or periodically act onto the surface of the patient's body so as to administer the non-acoustic stimuli to the patient's body. By doing so, the non-acoustic stimulus to be administered to the patient's body constitute periodic or oscillating stimulus, i.e. which amplitude or stimulation intensity periodically varies over time.

More specifically, according to one configuration, the vibrotactile stimulating elements 14a-d comprise a rod or any other component configured for mechanically acting upon the patient's skin. For doing so, the stimulating elements 14a-d include an electro-mechanical actuator for converting electrical energy into a movement of the rod. For example, the electro-mechanical actuator may be an equal current motor, a voice coil, a piezo-electric transducer or a transformer built up of electro-active polymers which change their shape on the application of an electric current. For providing electrical energy to the electro-mechanical actuator, the stimulation unit 12 may comprise or be connected to an energy source, in particular provided in the form of a battery.

To that end, for providing the acoustic stimuli, the stimulation unit 12 further comprises respective acoustic stimulating elements 14 which are configured to generate the acoustic stimuli to be administered to the patient's inner ear.

Specifically, the acoustic stimulating elements 14 are configured to generate sound waves which are provided to the patient's inner ear through air and/or bone conduction so as to administer the acoustic stimuli.

In general, the acoustic stimulating elements 14 may be provided in the form of any suitable component capable of selectively generating sound waves. Accordingly, the acoustic stimulating element 14 may be provided in the form of a loudspeaker which may be provided separately from the band 18. In the shown configuration, the acoustic stimulating elements 14 are constituted by the vibrotactile stimulating elements 14a-d. In other words, each one of the stimulating elements 14a-d is configured to generate both the acoustic and the non-acoustic stimuli. Accordingly, the stimulation unit 12 is configured to simultaneously generate the acoustic stimulus and the non-acoustic stimulus upon oscillatingly or periodically actuating the respective stimulating elements 14a-d. In other words, the stimulation unit 12 is configured to generate the acoustic stimulus upon generating the non-acoustic stimulus. By doing so, each one of the stimulating elements 14a-d is configured to, upon actuation, provide a set of stimuli constituted by a non-acoustic stimulus and an associated acoustic stimulus. Accordingly, each acoustic stimulus is associated to one non-acoustic stimulus, wherein the stimulation unit 12, i.e. each one of the stimulating elements 14a-d, is configured to generate one non-acoustic stimulus together with the associated acoustic stimulus.

Specifically, the stimulation unit 12 is provided such that each one of the plurality of stimulating elements 14a-d is actuated at an actuation frequency v in the range of human hearing, i.e. in the range between 20 Hz to 20 kHz. For example, the stimulating elements 14 are actuated at an actuation frequency v in the range of 20 Hz to 250 Hz. Alternatively or additionally, the stimulating elements 14a-d may be actuated in frequency ranges associated with low-frequency tones, i.e. between 200 Hz to 600 Hz or between 330 Hz to 600 Hz, which may be perceived to be relaxing and pleasant by the patient. Specifically, the stimulating elements 14a-d are configured such that they can be selectively and variedly actuated at different actuation frequencies among the indicated frequency ranges.

Figure 4:
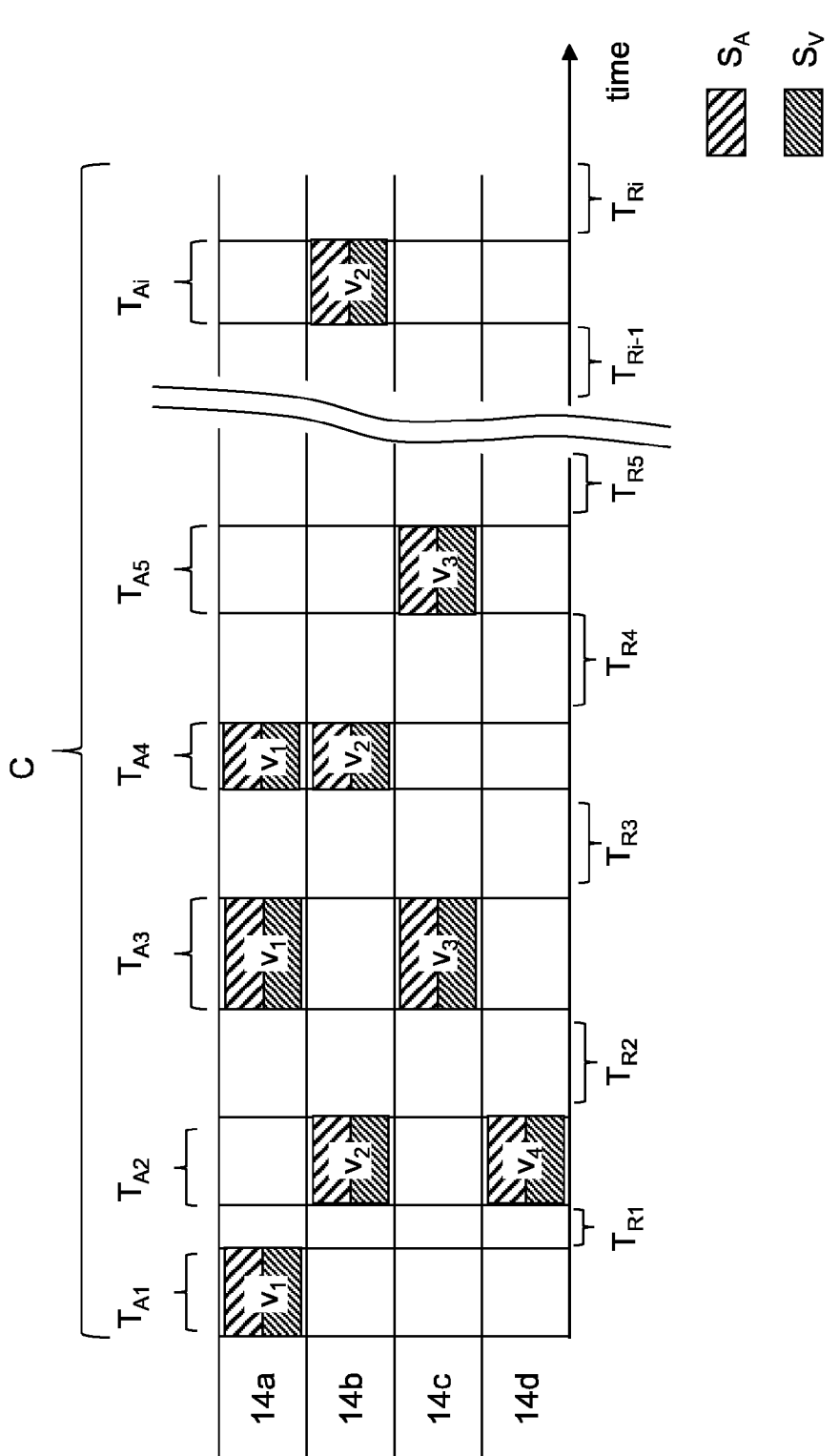
FIG. 4 schematically shows a sequence of actuating periods according to a first configuration, according to which non-invasive stimulating elements of the medical treatment device are actuated to suppress the pathologically synchronous activity.

In the following, with reference to FIG. 4, operation of the medical treatment device 10, i.e. its stimulation unit 12, is specified in more detail. During operation, the control unit 16 is configured to selectively and intermittently actuate the different stimulating elements 14a-d. Specifically, the control unit 16 is configured for actuating the stimulating elements 14a-d in a sequence C of successive actuating periods $T_{A1-Ai}$, wherein character "i" refers to a total number of actuating periods within a sequence C. FIG. 4 shows the sequence C of successive actuating periods $T_{A1-Ai}$; which forms a control sequence or control pattern illustrating the actuation of the respective actuating elements 14a-d over time. Specifically, in FIG. 4, the actuation of the respective stimulating elements 14a-d is illustrated by means of dashed fields positioned within the actuating periods $T_A$.

The sequence C comprises the number i of time shifted, non-overlapping actuating periods $T_{A1-Ai}$, during which at least one of the stimulating elements 14a-d is actuated to generate both the acoustic stimuli $S_A$ and the non-acoustic, vibrotactile stimuli $S_V$. For distinguishing between acoustic and non-acoustic stimuli $S_A$, $S_V$ to be generated by the respective stimulating elements 14a-d, different pattern of the dashed fields, i.e. as regards their orientation and line thickness, are selected as indicated by the legend in FIG. 4. The duration of the actuating periods $T_{A1-Ai}$, corresponds to a length of the corresponding stimuli $S_A$, $S_V$ generated by the stimulation elements 14a-d. For example, the actuating periods may have a duration between 25 ms to 3 s, in particular 100 ms or 125 ms.

Between the successive actuating period $T_{A1-Ai}$, resting periods $T_{R1-Ri}$, are scheduled, during which the patient's body is not subjected to stimuli generated by the stimulation unit 12. The length of the resting periods $T_{R1-Ri}$, may vary or be constant during the sequence C. Further, the length of the resting period $T_R$ may be 0 s such that two successive actuating periods directly follow one after the other. In an alternative configuration, the actuating periods within the sequence may at least partially overlap.

During an actuating period $T_A$, the control unit 16 may be configured to actuate exclusively one of the stimulating elements 14a-d or to simultaneously actuate more than one stimulating elements 14a-d. In one configuration, the control unit 16 is configured to variedly determine for each actuating period $T_A$ a number of n stimulating elements 14a-d to be simultaneously actuated during the respective actuating periods $T_A$. In this context, the term "variedly" means that the values for the number n diversely, in particular non-periodically, varies across the sequence C. Specifically, the parameter n is an integer greater than 1. If n equals 1, this means that during the respective actuating period $T_A$ exclusively one of the stimulating elements 14a-d is actuated. If n is greater than 1, this means that more than one, i.e. n, stimulating elements 14a-d are actuated simultaneously during the respective actuating period $T_A$.

As regards the specific procedure and implementation of the control unit 16 for variedly determining the number n of different stimulating elements 14a-d to be simultaneously actuated during the respective actuating periods $T_A$ and for determining the length of the actuating periods $T_A$ and the corresponding resting periods $T_R$, explicit reference is made to the published International Application WO 2019/243634 A1. Specifically, the control unit 16 may employ at least one of a deterministic, a stochastic, a chaotic and a (pseudo-) random algorithm method for variedly determining the number n of different stimulating elements 14a-d to be simultaneously actuated during the respective actuating periods $T_A$ and for determining the length of the actuating periods $T_A$ and the corresponding resting periods $T_R$.

As can be gathered from FIG. 4, each stimulating element 14a-d simultaneously generates acoustic and vibrotactile stimuli $S_A$, $S_V$ when being actuated at a predefined frequency $v_{1-4}$. The stimulation unit 12, i.e. its control unit 16, is configured to operate the different stimulating elements 14a-d at different actuating frequencies $v_{1-4}$. In other words, in the shown configuration, the actuation frequency at which the respective stimulating elements 14a-d are to be actuated differs among the set of different stimulating elements 14a-d.

Each stimulating element 14a-d is actuated at a substantially constant and the same actuation frequency $v_{1-4}$ during the sequence C. Specifically, when being actuated by the control unit 16, a first stimulating element 14a is operated at a first actuation frequency $v_1$, a second stimulating element 14 is operated at the second actuation frequency $v_2$, a third stimulating element 14c is operated at a third actuation frequency $v_3$ and a fourth stimulating element 14d is operated at a fourth actuation frequency $v_4$.

More specifically, the stimulation unit 12 is configured such that the actuating frequencies $v_1$-4, at which the stimulating elements 14a-d are to be actuated, in particular simultaneously actuated, are adjusted to a music scale. In other words, the stimulation unit 12 may be provided with a predetermined set of actuation frequencies $v_1$-4, at which the individual stimulating elements 14a-d can be actuated, wherein the actuation frequencies $v_1$-4, i.e. the individual members of the set of actuation frequencies, constitute, in particular substantially constitute, at least a part of a music scale. In this way, effectivity of the treatment as well as acceptability of the patient to the treatment may be improved.

To further increase effectivity of the treatment and/or acceptability of the patient to the treatment, the actuation frequencies are adjusted to consonant frequencies of a music scale.

In a further development, the stimulation unit 12 may be configured such that the actuating frequencies $v_{1-4}$, i.e. the individual members of the set of actuation frequencies, are adjusted to a pentatonic scale. In this way, particularly acceptable, smooth and/or relaxing acoustic stimulus sequences may be provided. Further, pentatonic frequencies may provide the advantageous effect that they can be smoothly combined.

Specifically, the stimulation unit 12 may be provided with a set of different actuation frequencies $v_{1-5}$ which constitute at least a part of the pentatonic scale. Starting from a first actuation frequency $v_1$, the other frequencies to be included into the set of actuating frequencies may be determined or calculated based on at least one of the following equations (1) to (4):

$$v_2 = v_1 * \% ,\tag{1}$$

$$v_3 = v_1 * 5/4 ,\tag{2}$$

$$v_4 = v_1 * 3/2, \text{ and} \tag{3}$$

$$v_5 = v_1 * 5/3 ,\tag{4}$$

wherein in particular vi may have a value of, for example, 200 Hz or 220 Hz or any other value, in particular in the range of 200 Hz to 600 Hz. To that end, vi may be a piano key frequency or any other musical instrument frequency.

In the context of the proposed medical treatment device 10, it has been found that the above advantageous effects may also be achieved by using octaves of individual members comprised in the set of actuation frequencies. Thus, alternatively or additionally, further actuating frequencies to be included into the set of actuation frequencies may be calculated based on at least one of the following equations:

$$v_6 = 2^{k*} v_1 ,\tag{5}$$

$$v_7 = 2^{k*} v_2 ,\tag{6}$$

$$v_8 = 2^{k*} v_3 ,\tag{7}$$

$$v_9 = 2^{k*} v_4, \text{ and} \tag{8}$$

$$v_{10} = 2^{k*} v_5 ,\tag{9}$$

wherein k is a natural number equal to or greater than 1, such as 1, 2, 3 or 4.

Furthermore, the stimulation unit 12 may be configured to adjust a vibration amplitude of each one of the different stimulating elements 14a-d. Specifically, the stimulation unit 12 may be configured to adjust the vibration amplitude of each one of the different stimulating elements 14a-d in dependence on a patient's perception in view of the acoustic or non-acoustic stimuli $S_A$, $S_V$. For doing so, the stimulation unit 12 may be configured to adjust the vibration amplitude of each one of the different stimulating elements 14a-d in dependence on at least one of an equal proprioceptive perception, an equal loudness perception or any other parameters being indicative of the patient's perception in view of the acoustic and non-acoustic stimuli $S_A$, $S_V$.

As set forth above, in the configuration depicted in FIG. 4, the stimulation unit 12 is configured such that the actuation frequency of each one of the stimulating elements 14a-d remains constant or un-changed during operation, i.e. during the sequence C of actuating periods $T_A$.

In a further development, the stimulation unit 12 may be configured to actuate at least one stimulating element 14a-d at different stimulating frequencies v. In other words, the stimulating unit 12 may be configured such that an actuation frequency of at least one stimulating element 14a-d is varied over time. For example, the stimulating unit 12 may be configured such that the actuation frequency of at least one stimulating element 14a-d is varied during an actuating period $T_A$. Alternatively or additionally, the stimulating unit 12 may be configured such that the actuation frequency of at least one stimulating element 14a-d remains constant during an actuating period $T_A$, but is varied among the sequence C, i.e. among successive actuating periods $T_A$. This means that, for example, the first stimulating element 14a may be operated at the first actuation frequency vi during a first actuating period $T_{A1}$ and may be operated at a different actuation frequency, e.g. the second, third or fourth actuation frequency $v_{2-4}$ or any other actuating frequency, in another actuating period $T_A$. Specifically, the actuation frequency of respective stimulating elements 14a-d may be varied such that it is successively increased or decreased, in particular by being successively adjusted to increasing or decreasing frequencies included in the predefined set of actuating frequencies.

In one configuration, the stimulation unit 12 may be configured to variedly select for each stimulating element 14a-d at which actuation frequency comprised in the predetermined set of actuating frequencies the stimulating element 14a-d is to be actuated during a corresponding actuating period $T_A$. Specifically, for doing so, the control unit 12 may be configured to stochastically and/or deterministically and/or combined stochastically-deterministically and/or determine for each stimulating element 14a-d at which actuation frequency comprised in the predetermined set of actuating frequencies the stimulating element 14a-d is to be actuated during a corresponding actuating period $T_A$. To that end, in such a configuration, the control unit 16 may be configured to ensure that, within each one of the actuating periods $T_A$, the stimulating elements 14a-d are operated at different actuating frequencies.

Figure 5:
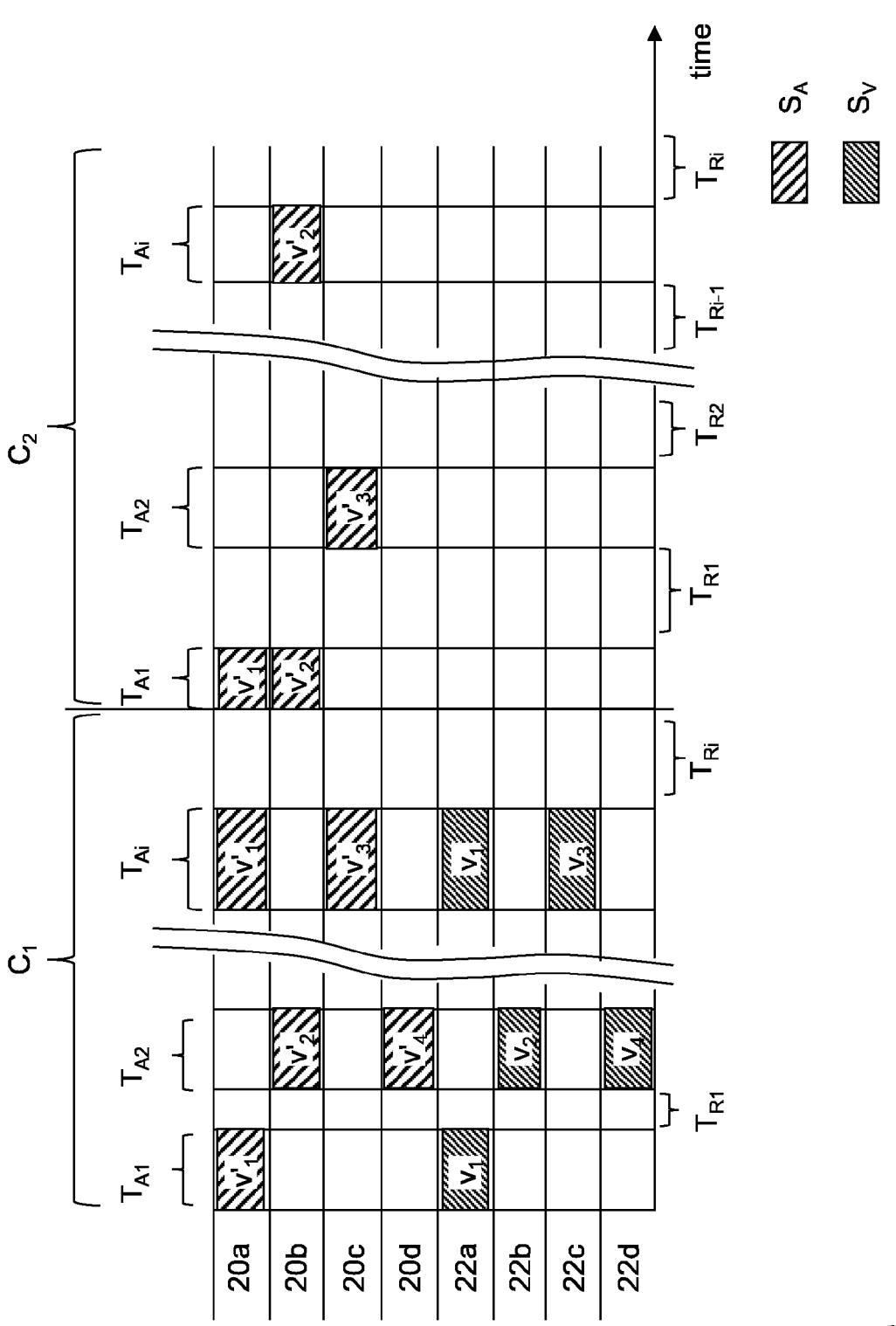
FIG. 5 schematically shows a further sequence of actuating periods according to a second configuration.

FIG. 5 illustrates operation of the medical treatment device 10 according to another configuration. In this configuration, the medical treatment device 10 comprises a set of first actuating elements 20a-d configured to generate the acoustic stimuli $S_A$ for suppressing the pathologically synchronous activity of the neurons and a set of second actuating elements 22a-d configured to generate the non-acoustic, vibrotactile stimuli $S_A$ for suppressing the pathologically synchronous activity of the neurons. The first stimulating elements 20a-d and the second stimulating elements 22a-d constitute separate components of the stimulating unit 12. The first stimulating elements 20a-d may be provided by a single component, e.g. provided in the form of a loudspeaker which is configured to simultaneously generate a plurality of acoustic stimuli.

In this configuration, the control unit 16 is configured to operate the stimulation unit 12 in a first operating mode illustrated by sequence C1 in FIG. 5 and in a second operating mode illustrated by sequence C3 in FIG. 5.

Specifically, in the first operating mode, the control unit 16 is configured to operate the stimulation unit 12 such that the generation of the acoustic stimuli $S_A$ is paired or linked to the generation of the non-acoustic stimuli. Accordingly, the control unit 16 is configured to control the first and the second actuating elements 20a-d, 22a-d such that non-acoustic stimuli $S_V$ are generated simultaneously or together with their associated acoustic stimuli $S_A$. Each first stimulating element 20a-d is associated to one of the second stimulating elements 22a-d in such a way that a first stimulating element 20a-d and its associated second stimulating element 22a-d generate a corresponding set of stimuli constituted by the non-acoustic stimulus $S_V$ and its associated acoustic stimulus $S_A$. As can be gathered from FIG. 5, in the shown configuration, the following pairs of first and second stimulating elements are actuated simultaneously and thus associated to one another: 20a-22a; 20b-22b; 20c-22c; and 20d-22d.

The first stimulating elements 20a-d are actuated at an actuation frequency v' which dependence on the actuation frequency v of their associated second stimulating elements 22a-d. Specifically, each first stimulating element 20a-d may be actuated at an actuation frequency v' which is equal to or which constitutes a harmonic of the actuation frequency v of its associated second stimulating element 22a-d. Accordingly, the actuation frequency v' of each first stimulating element 20a-d may be 1/m or m/1 of the actuation frequency v of its associated second stimulating element 22a-d, wherein m is a natural number greater than 1. Further, a frequency v" of a sound wave generated by the respective first stimulating element 20a-d and conducted to the patient's inner ear may be 1/m or m/1 of the actuation frequency v of the associated second stimulating element 22a-d. Alternatively or additionally, the actuation frequency v' of each first stimulating element 20a-d and/or the frequency v" of the sound wave generated by the respective first stimulating element 20a-d and the actuation frequency v of the associated second stimulating element 22a-d may be adjusted to a pentatonic scale. In other words, the actuation frequency v' and/or the frequency v" and the actuation frequency v of the associated second stimulating element 22a-d may constitute a part of a pentatonic scale. Thus, the actuation frequency v' and/or the frequency v" may correlate to the actuation frequency v of the associated second stimulating element 22a-d or may be calculated based on at least one of the following equations (10) to (14):

$$v'/'' = v*2^I, \tag{10}$$

$$v'/'' = v*2^{I}*9/8, \tag{11}$$

$$v'/'' = v*2^{I}*5/4, \tag{12}$$

$$v'/'' = v*2^{I}*3/2, \text{ and} \tag{13}$$

$$v'/'' = v*2^{I}*5/3, \tag{14}$$

wherein v'/" refers to the actuation frequency v' of each first stimulating element 20a-d and/or the frequency v" of the sound wave generated by the respective first stimulating element 20a-d; wherein v refers to the actuation frequency of the associated second stimulating element 22a-d; and I refers to a natural number equal to or greater than 0.

To that end, in the second operating mode of the stimulation unit 12, the control unit 16 is configured to operate the first and the second stimulating elements 20a-d, 22a-d such that the acoustic stimuli $S_A$ are generated decoupled from the generation of the non-acoustic stimuli $S_V$. As can be gathered from FIG. 5, in the second operating mode, i.e. within the second sequence C2, the patient is not subjected to the non-acoustic stimuli $S_V$.

In the second operating mode, the control unit 16 is configured to variedly determine the number n of first stimulating elements 20a-d to be simultaneously actuated during the respective actuating period $T_A$ and to variedly select which one of the first stimulating elements 20a-d are to be actuated during that actuating period $T_A$. For doing so, the control unit 16 may be configured to stochastically and/or deterministically and/or combined stochastically-deterministically determine the number n of first stimulating elements 20a-d to be actuated simultaneously during the respective actuating periods $T_A$. Further, the control unit 16 may be configured to stochastically and/or deterministically and/or combined stochastically-deterministically select which one of the first stimulating elements 20a-d are to be actuated during the respective actuating period $T_A$.

By operating the stimulation unit 12 in the first operating mode, principles of condition and/or associative learning may be employed for effectively down-regulating abnormal synaptic weights. More specifically, by combining acoustic with non-acoustic stimuli, the conditioning or associative learning may be provided in a particular natural manner, thereby increasing acceptability of the patient to the treatment.

In the proposed medical treatment device 10 according to any one of the above described configuration, all actuation frequencies, i.e. at which the different stimulating element 14; 20a-d, 22a-d are operated, correlate in a predefined manner to one another, in particular so as to be adjusted to a pentatonic scale. For doing so, a basic actuating frequency $v_0$ of a one of the stimulating elements, in particular of one of the second stimulating elements 22a-d, may be determined or provided based on which all other actuating frequencies of the residual stimulating elements are adjusted. For doing so, the other actuating frequencies v may be correlated to the basic actuating frequency $v_0$ based on at least one of the following equations (15) to (19):

$$v = v_0*2^I, \tag{15}$$

$$v = v_0*2^{I}*9/8, \tag{16}$$

$$v = v_0*2^{I}*5/4, \tag{17}$$

$$v = v_0*2^{I}*3/2, \text{ and} \tag{18}$$

$$v = v_0*2^{I}*5/3, \tag{19}$$

wherein I refers to a natural number equal to or greater than 0. Further, it is noted that the actuating frequency of the stimulating element 14; 22a-d configured to generate the acoustic stimuli may refer, in particular be equal to, a frequency of the sound wave generated by that stimulating element and conducted to the patient's inner ear.

It will be obvious for a person skilled in the art that these embodiments and items only depict examples of a plurality of possibilities. Hence, the embodiments shown here should not be understood to form a limitation of these features and configurations. Any possible combination and configuration of the described features can be chosen according to the scope of the invention.

This is in particular the case with respect to the following optional features which may be combined with some or all embodiments, items and/or features mentioned before in any technically feasible combination.

A medical treatment device for stimulating neurons of a patient to suppress a pathological synchronous activity of the neurons is provided. The medical treatment device comprises a non-invasive stimulation unit configured for simultaneously administering at least one acoustic stimulus and at least one non-acoustic stimulus to a patient's body, each of which is configured to suppress the pathologically synchronous activity when being administered to the patient's body.

As set forth above, an abnormally strong synchronous activity of neurons, which induces several brain diseases, i.e. Parkinson's diseases, may be caused by abnormally upregu-lated synaptic connections. To counteract abnormal neuronal synchronization processes in a long-lasting, sustained man-ner, it is particularly favorable to downregulate the synaptic weights.

It has been found that effective down-regulation of abnor-mal synaptic weights can be achieved by mutually activa-tions of neuronal populations with stimulus of varying composition, i.e. in terms of location and modality. Accord-ingly, by providing the medical treatment device which is configured to simultaneously administer at least one acoustic stimulus and at least one non-acoustic stimulus for suppress-ing the pathologically synchronous activity, the proposed device enables to effectively suppress pathologically syn-chronous activity of the neurons, i.e. by desynchronizing the pathologically synchronous activity of the neurons.

Specifically, the medical treatment device may be con-figured to be fastened to a patient's head, wherein in a fastened state of the medical treatment device in which it is fastened to the patient's head, the stimulating unit may be configured to provide the acoustic stimulus to a patient's ear and the non-acoustic stimulus to a patient's skin in the region of the patient's forehead, in particular the first branch of the trigeminal nerve. Alternatively or additionally, the stimulating unit may be configured to provide the non-acoustic stimulus to a patient's skin in the region of the patient's occiput, in particular to the C2 or C3 dermatome.

In a further development, the stimulation unit may be provided such that the acoustic stimulus is configured to suppress a pathologically synchronous activity of a first neuronal population, in particular in at least one of a patient's brain or spinal cord, when being administered to the patient's body. Alternatively or additionally, the non-acoustic stimulus may be configured to suppress a patho-logically synchronous activity of a second neuronal popu-lation, in particular in at least one of a patient's brain or spinal cord, which is different or delimited from the first neuronal population when being administered to the patient's body.

Specifically, the at least one non-acoustic stimulus is a mechanical stimulus, in particular a vibrotactile stimulus.

In a further development, each one of the at least one acoustic stimulus may be associated to one non-acoustic stimulus. Further, the stimulation unit may be configured to simultaneously generate one non-acoustic stimulus together with its associated acoustic stimulus.

The stimulating unit may comprise at least one vibrotac-tile stimulating element which is configured to oscillatingly or periodically act onto a surface of the patient's body so as to administer the non-acoustic stimulus to the patient's body.

In a further development, the stimulation unit may con-figured to simultaneously generate the acoustic stimulus and the non-acoustic stimulus upon oscillatingly or periodically actuating the vibrotactile stimulating element. Alternatively, the stimulating unit may comprise at least one acoustic stimulating element for generating the acoustic stimuli. The acoustic stimulating element may be provided separately from the vibratory stimulating element. Further, the stimulation unit may be configured to simultaneously actuate the vibrotactile stimulating element and the acoustic stimulating element so as to simultaneously generate the non-acoustic and acoustic stimuli.

The vibrotactile stimulating element and the acoustic stimulating element may be actuated at an actuation fre-quency in the range of 20 Hz to 20 kHz, in particular from 20 Hz to 250 Hz or from 200 Hz to 600 Hz.

The stimulation unit may comprise at least two vibrotac-tile stimulating elements or any other stimulating elements for generating the non-acoustic and/or acoustic stimuli. Each one of the at least two stimulating elements may be config-ured to generate one of at least two non-acoustic stimuli, and wherein the stimulation unit is configured to operate the at least two stimulating elements at different actuation or vibration frequencies. In a further development, the actua-tion or vibration frequencies, at which the stimulating ele-ments are to be actuated, may be adjusted to a music scale, in particular a pentatonic scale.

Further, the stimulation unit may be provided with a set of different actuation frequencies. This set of actuating fre-quencies may include actuating frequencies, in particular predefined actuating frequencies, at which the at least one stimulating element can be actuated. In other words, the stimulating elements may be configured to be actuated at the actuating frequencies comprised in the set of actuating frequencies. Accordingly, the stimulating elements may be not allowed to be operated at actuation frequencies which are not comprised in the set of actuating frequencies.

The set of actuation frequencies may comprise a first actuating frequency and at least one further actuating fre-quency which is determined in dependence on or correlates to the first actuating frequency. In this way, upon determin-ing the first actuating frequency, also the at least one further actuating frequency may be determined.

Specifically, the at least one further actuating frequency of the set of different actuation frequencies may correlate to the first actuating frequency or may be determined in depen-dence on the first actuating frequency according to at least one of the following equations (20) to (28):

$$v_2 = v_1 * 9\!/\!8, \tag{20}$$

$$v_3 = v_1 * 5\!/\!4, \tag{21}$$

$$v_4 = v_1 * 3\!/\!2, \tag{22}$$

$$v_5 = v_1 * 5\!/\!3, \tag{23}$$

$$v_6 = v_1 * 2^k, \tag{24}$$

$$v_7 = v_1 * 2^k * 9\!/\!8, \tag{25}$$

$$v_8 = v_1 * 2^k * 5\!/\!4, \tag{26}$$

$$v_9 = v_1 * 2^k * 3\!/\!2, \text{ and} \tag{27}$$

$$v_{10} = v_1 * 2^k * 5\!/\!3, \tag{28}$$

wherein $v_1$ refers to the first actuating frequency; each one of $v_2$ to $v_{10}$ refers to the at least one further actuating frequency; and k refers to a natural number equal to or greater than 1.

In a further development, the stimulation unit may com-prise at least one first stimulating element configured for administering the at least one acoustic stimulus and at least one second stimulating element configured for administer-ing the at least one non-acoustic stimulus, wherein each first stimulating element is associated to one of the at least one second stimulating element in such a way that the first stimulating element and the associated second stimulating element are actuable so as to simultaneously generate the acoustic stimulus and the non-acoustic stimulus.

Additionally or alternatively, the stimulation unit may comprise a control unit for controlling operation of the stimulation unit, in particular its stimulating elements. Specifically, the control unit may be configured to operate the stimulation unit in a first operating mode in which the generation of the acoustic stimuli is linked or paired to the generation of the non-acoustic stimuli, and in a second operating mode in which the generation of the acoustic stimulate is decoupled from the generation of the non-acoustic stimuli.

Furthermore, a medical treatment method for stimulating neurons of a patient to suppress a pathologically synchronous activity of the neurons is provide. The method comprises the step of non-invasively and simultaneously administer at least one acoustic stimulus and at least one non-acoustic stimulus to a patient's body, each of which is configured to suppress the pathologically synchronous activity.

LIST OF REFERENCE NUMERALS

10 Medical treatment device
12 Stimulation unit
14 Stimulating element
16 control unit
18 band
20 Stimulating element for generating acoustic stimuli
22 Stimulating element for generating non-acoustic stimuli
C Sequence of actuating periods
$S_A$ acoustic stimulus
$S_V$ non-acoustic stimulus
$T_A$ Actuating period
$T_R$ Resting period
v actuating frequency
The invention claimed is:

1. A medical treatment device for stimulating neurons of a patient to suppress a pathologically synchronous activity of the neurons, comprising a non-invasive stimulation unit configured for simultaneously administering at least one acoustic stimulus and at least one non-acoustic stimulus to a patient's body, each of which is configured to suppress the pathologically synchronous activity when being administered to the patient's body, wherein the stimulation unit comprises a vibrotactile stimulating element which is configured to oscillatingly or periodically act onto a surface of the patient's body so as to simultaneously administer the non-acoustic stimulus and the acoustic stimulus to the patient's body, wherein the stimulation unit is configured to simultaneously generate the acoustic stimulus and the non-acoustic stimulus upon oscillatingly or periodically actuating the vibrotactile stimulating element, wherein when being administered to the patient's body, the acoustic stimulus is configured to suppress a pathologically synchronous activity of a first neuronal population, in particular in at least one of a patient's brain or spinal cord, and the non-acoustic stimulus is configured to suppress a pathologically synchronous activity of a second neuronal population, in particular in at least one of a patient's brain or spinal cord, which is different or delimited from the first neuronal population.

2. The medical treatment device according to claim 1, which is configured to be fastened to a patient's head, wherein in a fastened state of the medical treatment device in which it is fastened to the patient's head, the stimulating unit is configured to provide the acoustic stimulus to a patient's ear and the non-acoustic stimulus to a patient's skin in a region of a forehead of the patient, in particular a first branch of a trigeminal nerve, or occiput, in particular a C2 or C3 dermatome.

3. The medical treatment device according to claim 1, wherein the at least one non-acoustic stimulus is a vibrotactile stimulus.

4. The medical treatment device according to any one of claim 1, wherein each one of the at least one acoustic stimulus is associated to one non-acoustic stimulus, and wherein the stimulation unit is configured to simultaneously generate one non-acoustic stimulus together with its associated acoustic stimulus.

5. The medical treatment device according to claim 1, wherein the vibrotactile stimulating element is actuated at an actuation frequency in a range of 20 Hz to 20 kHz, in particular from 20 Hz to 250 Hz or from 200 Hz to 600 Hz.

6. The medical treatment device according to claim 1, wherein the stimulation unit comprises at least two vibrotactile stimulating elements, each of which is configured to generate one of at least two non-acoustic stimuli, and wherein the stimulation unit is configured to operate the at least two stimulating elements at different actuation frequencies.

7. The medical treatment device according to claim 6, wherein the actuation frequencies, at which stimulating elements are to be actuated, are adjusted to a music scale, in particular a pentatonic scale.

8. The medical treatment device according to claim 1, wherein the stimulation unit is provided with a set of different actuation frequencies including frequencies at which the stimulating element is to be actuated, and wherein the set of different actuation frequencies comprises a first actuating frequency and at least one further actuating frequency which is determined in dependence on or correlates to the first actuating frequency.

9. The medical treatment device according to claim 8, wherein the at least one further actuating frequency of the set of different actuation frequencies correlates to the first actuating frequency according to at least one of the following equations:

$$v_2 = v_1 * 9/8,$$

$$v_3 = v_1 * 5/4,$$

$$v_4 = v_1 * 3/2,$$

$$v_5 = v_1 * 5/3,$$

$$v_6 = v_1 * 2^k,$$

$$v_7 = v_1 * 2^k * 9/8,$$

$$v_8 = v_1 * 2^k * 5/4,$$

$$v_9 = v_1 * 2^k * 3/2, \text{ and}$$

$$v_{10} = v_1 * 2^k * 5/3,$$

wherein $v_1$ refers to the first actuating frequency; each one of $v_2$ to $v_{10}$ refers to the at least one further actuating frequency; and k refers to a natural number equal to or greater than 2.

10. The medical treatment device according to claim 1, wherein the stimulation unit comprises a plurality of vibrotactile stimulating elements, wherein each of the stimulating elements is configured to oscillatingly or periodically act onto a surface of the patient's body so as to simultaneously administer non-acoustic stimulus and acoustic stimulus to the patient's body.

\* \* \* \* \*